United States Patent [19]

Kato et al.

[11] Patent Number: 4,924,085
[45] Date of Patent: May 8, 1990

[54] UNEVEN-SURFACE DATA DETECTION APPARATUS

[75] Inventors: Masayuji Kato, Atsugi; Seigo Igaki, Inagi; Fumio Yamagishi, Ebina; Hiroyuki Ikeda, Yokohama; Takashi Shinzaki; Shin Eguchi, both of Atsugi, all of Japan

[73] Assignee: Fujitsu Limited, Kawasaki, Japan

[21] Appl. No.: 370,768

[22] Filed: Jun. 23, 1989

[30] Foreign Application Priority Data

Jun. 23, 1988 [JP] Japan .................. 63-155670
Aug. 12, 1988 [JP] Japan .................. 63-201674
Dec. 16, 1988 [JP] Japan .................. 63-317747
Dec. 28, 1988 [JP] Japan .................. 63-331560

[51] Int. Cl.$^5$ ............................. H01J 5/16
[52] U.S. Cl. .................. 250/227.28; 356/71; 250/227.31; 250/227.32
[58] Field of Search .............. 250/271, 227, 556; 356/71; 382/4, 5

[56] References Cited

U.S. PATENT DOCUMENTS

3,975,711  8/1976  McMahon ..................... 356/71
4,684,802  8/1987  Hakenewerth ................. 382/4
4,728,186  3/1988  Eguchi et al. .
4,785,171  11/1988  Dowling, Jr. et al. .......... 356/71

Primary Examiner—David C. Nelms
Attorney, Agent, or Firm—Staas & Halsey

[57] ABSTRACT

An uneven surface data detection apparatus for detecting an uneven surface, such as a human finger, having projected portions and recessed portions. A transparent base having upper and lower surfaces and an upper surface defining an uneven surface contact portion is provided, and a light is incident on the uneven surface so that the light derived from the recess portions enters to the transparent base and comes out thereof. However, a part of the light derived from the projected portions is totally reflected at least one time by the lower opposite surface and focussing lens is integrally formed on the transparent base so that the totally reflected light is drawn out of transparent base and enters to an image sensor.

27 Claims, 10 Drawing Sheets

UNEVEN-SURFACE DATA DETECTION APPARATUS

BACKGROUND OF THE INVENTION

1. Field of the Invention

This invention relates to an apparatus for detecting data of an uneven surface, such as human fingerprint and the like, in a personnel identification apparatus. More particularly, this invention relates to an uneven surface data detection apparatus having a thin structure.

2. Description of the Related Art

In today's high-tech world of information, a strong demand has arisen for better computer system security techniques. In particular, to protect confidential data, a reliable identification must be made of personnel in charge of such systems, and thus strict checks upon entrance to a computer room have become very important. In the past, passwords and identification (ID) cards have been used, and now personal identification systems using fingerprints are increasingly used.

In a first conventional method for entering uneven surface data (e.g., a fingerprint), a fingerprint is printed on paper using ink and is then sensed using an image sensor. In this case, however, a finger must be stained with ink each time the fingerprint data is to be entered, and any uneven coating or blurring of the ink greatly hinders the input operation.

In a second conventional method, a light beam is incident on a glass/air interface at a critical angle or larger, and thus an uneven surface pattern is instantaneously obtained. In this method, such as seen from FIG. 21, an uneven surface data detection apparatus uses a prism 2, a finger surface (uneven surface) pattern of a finger 1 having projections (ridges) 6 and recesses (grooves) 5 is pressed against an oblique side portion of the prism 2, and light from a light source 3 is made incident on an oblique side portion thereof at a critical angle or larger. The incident light is scattered by the projections 6 and is totally reflected by the glass/air interface in the recesses 5, and is then incident on a detector (e.g., an imaging element) 4, to thereby detect the uneven surface pattern. Nevertheless, light leaks through an unclean oblique surface caused by remaining fingerprints or moisture, and this leakage light irradiates the recessed portions 5 of the fingerprint and is scattered. Therefore, the level of the signal light from the projected portions 6 is lowered, and thus the contrast of the uneven surface pattern is also lowered. Further, since a prism is used, the total thickness of the apparatus cannot be reduced.

In a third known method, such as seen from FIG. 22 (and disclosed such as in U.S. Pat. No. 4,728,186), the apparatus includes a transparent body 7 made of glass or plastic and having a lower surface 7-1 and an upper surface 7-2 parallel to each other, and a diffraction grading 8 including a lens. A finger surface (uneven surface) pattern of a finger is pressed against one of the surfaces, i.e., the upper surface 7-2, and light is irradiated from the lower surface 7-1 in a direction substantially perpendicular to the transparent body 7. Air layers exist in the recess 5 of the finger, so that the light which enters the recess 5 is reflected at positions on the surface of the recess 5 and scattered in random directions. Most of the light again enters the transparent base 7 is discharged from the other surface 7-1, at the same angle as the light enters to the base 7. On the other hand, the light which reaches the convex 6 is scattered into the transparent base 7, so that a part of the light is discharged from the transparent base 7 as shown at R2, and the remaining is totally reflected and transmitted through the transparent base 7 as shown at R3. The light R3 is derived from the diffraction grading 8 and enters to an image sensor 4, such as a CCD, in which an image of the fingerprint can be obtained.

In the known fingerprint detection apparatus as shown in FIGS. 21 and 22, the optical elements, such as an image sensor, a diffraction grating, or the like, must be located opposite to and spaced from the fingerprint contact surface, and therefore, a relatively large space is required for obtaining the image data of the fingerprint. That is, an apparatus known in the prior art must have a relatively large thickness, and this makes it difficult to incorporate such a fingerprint detection apparatus in a door, a keyboard of computer terminals or the like.

SUMMARY OF THE INVENTION

An object of the present invention is to provide an uneven surface data detection apparatus, such as a fingerprint detection apparatus, having a relatively thin thickness, so that such an apparatus can be easily incorporated in a door, a keyboard of computer terminals or the like.

Another object of the present invention is to provide an uneven surface data detection apparatus, capable of overcoming the disadvantages mentioned above with reference to the related or prior art.

According to the present invention, there is provided an uneven surface data detection apparatus for detecting an uneven surface having projected portions and recessed portions, comprising: a transparent base having first and second surfaces, at least a part of said first surface defining an uneven surface contact portion; a light source for illuminating said uneven surface on said uneven surface contact portion, said light source simultaneously illuminating said projected portions and recessed portions of said uneven surface, so that the light derived from the recessed portions enters to the transparent base and comes out thereof, and at least a part of the light derived from the projected portions is totally reflected at least one time by the second surface opposite to said first surface; a focussing lens integrally formed on or integrally adhered to said transparent base, said focussing lens being located at a position for drawing said totally reflected light out of said transparent base; and an image sensor arranged outside of said transparent base for detecting an image of said uneven surface including said projected and recessed portions.

In the present invention, the focussing lens is integrally formed on or integrally adhered to the transparent base. Therefore, a thickness of this apparatus including an optical system can be reduced, and thus it is possible to incorporate such an apparatus in a door, a keyboard of computer terminals or the like.

The focussing lens comprises a convex lens. The apparatus preferably comprises: an iris diaphragm having an aperture, said iris diaphragm being arranged in such a manner that said aperture is located at a position corresponding to a center of the curvature of the radius of said convex lens, so that the light can be totally reflected at an area of said aperture. Such a total reflection preventing means may comprise a metal plate arranged in or adhered to said transparent base. Alternatively, such a total reflection preventing means may comprise a metal film formed by a vapor depositing of a metal, a rough surface, or a light absorbing paint film coated on said transparent base.

In one embodiment of this invention, said collimator lens comprises a cylindrical portion having one end integrally connected to said transparent base and the other end integrally formed with a convex lens portion.

In another embodiment, said transparent base has a third surface inclined to said first and second surfaces and said third surface is formed as a mirror surface, so that the light once totally reflected by said second surface is reflected by said mirror surface in such a manner that a propagation direction of the light reflected by said mirror surface is directed substantially parallel to said first and second surfaces.

In further embodiment, said apparatus further comprises a light shield box accommodating said image sensor, said shield box comprising a wall, a part of said wall being defined by said iris diaphragm. The total reflection preventing means comprises a metal plate adhered to said transparent base and said convex lens is adhered to said metal plate from the inside of said light shield box, in such a manner that said convex lens is integrally connected to said transparent base through said aperture. In still another embodiment, said apparatus further comprises a prism or second lens between said prism and said image sensor. The object to be detected may be a human finger having a fingerprint and said apparatus further comprises a guide member provided on said first surface for guiding the finger on said uneven surface contact portion, said guide member being incorporated with said light source, so that the light illuminates the uneven surface through said finger.

In the typical embodiments, the first and second surfaces of the transparent base are parallel to each other. However, in fact, the first and second surfaces are not always necessary to be parallel to each other, but the only necessity is that the light from the projected portions or ridges must be at least once totally reflected by the second, opposite surface.

DESCRIPTION OF THE PREFERRED EMBODIMENTS

Figure 1:
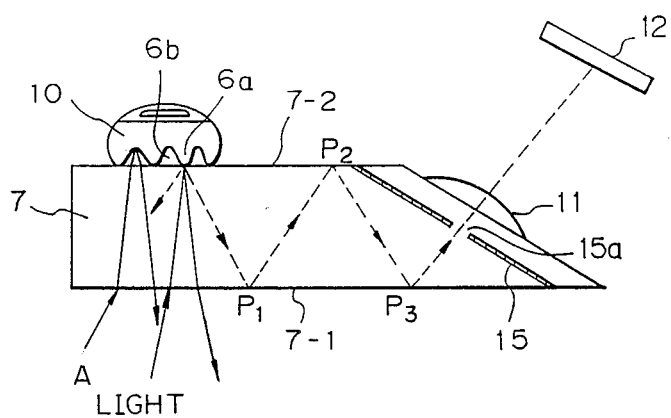
FIG. 1 is a schematic side view illustrating a principle of the structure of an uneven surface data (fingerprint) detection apparatus of this invention.

Referring now to the drawings, a basic principle of an uneven surface data detection apparatus according to the present invention will be described with reference to FIG. 1. An object having an uneven surface, such as a human finger 10, is pressed against a transparent or light transmission base 7 (e.g., glass) having a lower surface 7-1 and an upper surface 7-2 which are substantially parallel to each other. In FIG. 1, projected portions (ridges) 6a and recessed portions (grooves) 6b, which constitute a fingerprint of the finger 10, are emphasized. As can be seen from the drawing, the projected portions 6a are in contact with the upper surface 7-2, and the recessed portions 6b are separated from the upper surface 7-2 so that an air layer is formed between the recessed portions 6b and the upper surface 7-2. Light is radiated to the transparent base 7 from the lower surface side 7-1 thereof, as indicated by arrows A, and light entering the interior of the base 7 is randomly reflected by the projected portions 6a and is thereby scattered in all directions, since an air layer is not formed at the projected portions 6a. Scattered light beams which satisfy the total reflection condition of the base 7 (i.e., have an angle larger than a critical angle) are totally reflected by the lower surface 7-1 (at P1) of the base 7, as indicated by the dashed line in FIG. 1, totally reflected by the upper surface 7-2 (P2) thereof, totally reflected again by the lower surface 7-1 (at P3) thereof, and pass through a focussing lens 11 to be detected by an image sensor 12 arranged outside of the transparent base 7.

On the other hand, at the recessed portions 6b, light passes through out of the base 7, since an air layer is formed thereat. The light beams which reach the recessed portions 6b of finger 10 are randomly reflected by the surfaces of the recessed portions 6b, and are converted into scattered light. This scattered light again enters the base 7 from the upper surface 7-2 thereof and then externally discharged from the lower surface 7-1 of the base 7 at the same angle as the incident angle thereof, in accordance with Snell's law (as indicated by the solid line). Therefore, the scattered light from the recessed portions 6b is no longer transmitted through the interior of the base 7. Accordingly, only the totally reflected light transmitted through the interior of the base 7 is detected by the image sensor 12 to obtain an uneven surface pattern image.

Thus, the projection data and the recess data are discriminated depending on whether or not an air layer is formed between the transparent base 7 and the finger 10, since all the light components scattered by the recessed portions 6b are discharged outside the base 7 as indicated by the solid lines. On the other hand, the light components propagating through the interior of the base 7 correspond to the data from the projected portions 6a and must be detected only to obtain uneven surface pattern data with a good contrast.

The light components propagate through the interior of the base 7 and reach a position corresponding to the collimator lens 11 which is integrally formed on or integrally adhered to an inclined surface of the transparent base 7. Since the total reflection condition can be no longer satisfied at this position, the light components are guided through the focussing lens 11 and externally from the transparent base 7, and thus the pattern data from the light components of the projection 6a is then detected by the image sensor 12. A charge coupled device (CCD), such as SONY CORP., 018-L, can be advantageously used as such an image sensor 12.

In FIG. 1, the reference numeral 15 denotes an iris diaphragm 15 having an aperture 15a. The transparent base 7 can be made of any transparent or light transmissible material, such as glass or plastic. The image sensor 12 is arranged so that an input surface thereof is inclined to the propagation direction of the light entering the image sensor 12, to minimize aberration.

Figure 2:
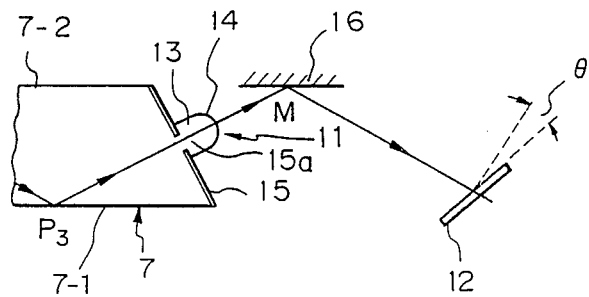
FIG. 2 is a side view of an embodiment of this invention.

FIG. 2 illustrates an embodiment of this invention, wherein a focussing lens 11 mounted on an inclined surface of the transparent base 7 comprises a cylindrical portion 13 having one end integrally connected to the transparent base 7 and the other end integrally formed with a convex lens portion 14. An iris diaphragm 15 having an opening aperture 15a is advantageously formed on the inclined surface of the transparent base 7 in such a manner that the aperture 15a is located at a position corresponding to a center of curvature of the radius of the convex lens portion 14, and thus the aperture 15a is positioned at a connecting portion between the transparent base 7 and the focussing lens 11.

In FIG. 2, the light discharged from the focussing lens 11 is reflected by a mirror 16 arranged outside of the transparent base 7 and then enters to the image sensor 12. In FIG. 2, when the finger 10 is placed on the uneven surface detection portion on the upper surface 7-2 of the transparent base 7, the light scattered by the projected portions 6a of the fingerprint is transmitted as shown by a dotted line and totally reflected at points P1, P2, and P3 in turn, focussed by the lens 11, and then reflected by the mirror 16.

Figure 3:
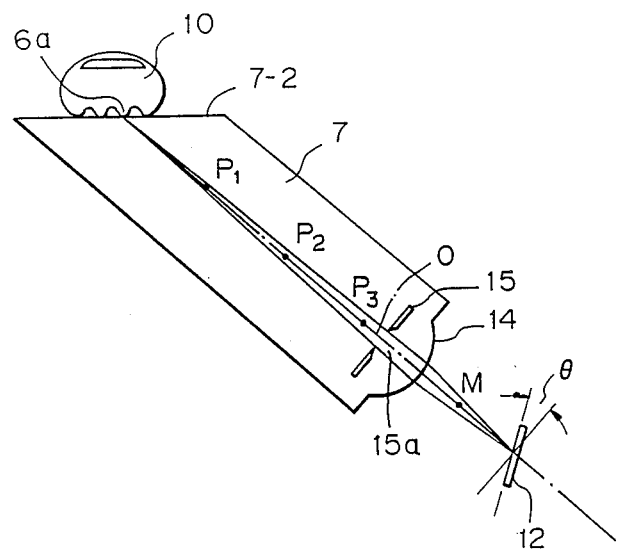
FIG. 3 is a schematic view illustrating an operation of an optical system in the embodiment shown in FIGS. 1 and 2.

FIG. 3 illustrates a straight optical path in the embodiment of FIG. 1 and FIG. 2. To simply explain the optical path of the light passing through the points P1, P2, and P3, and the mirror 16, the transparent base 7 can be shown as it is assumed to be developed along the scattered light path, under the condition that a straight light from the projection portions 6a of the fingerprint is assumed as an optical axis. Since one of the surfaces of the base 7, i.e., the upper surface 7-2 (the fingerprint detection surface), is inclined to the optical axis, it is understood that an input surface of the image sensor 12 also must be inclined.

It should be necessary to locate the opening aperture 15a at a position corresponding to a center of the curvature radius of the convex lens, due to a remarkable aberration which arises when focussing the light beam by a convex lens. In face, since the fingerprint input surface is inclined to the optical axis and, therefore, the length and breadth ratio of a fingerprint image is changed depending on the focal distance of the lens, it is necessary to take the change into consideration when dealing with the data input the image sensor 12.

Figure 4:
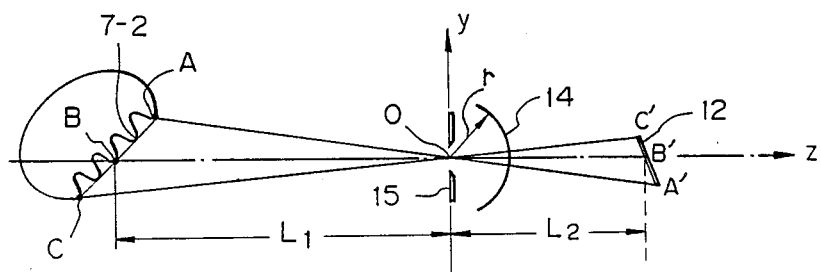
FIG. 4 is a view of the optical system shown in FIG. 3.

FIG. 4 is diagrammatical view of the optical system shown in FIG. 3 and illustrates the relationship between the fingerprint input surface and the image sensor surface, wherein the optical system uses a semi-spherical lens having a curvature radius r. In FIG. 4, assuming that an original point O is the center of the curvature radius r of the lens; the direction of the optical axis is z; the direction of the iris diaphragm providing with the opening aperture 15 is y; and the direction perpendicular to the y-axis and z-axis and perpendicular to the sheet, is x, then B refers to a point on the projected portions on the fingerprint input surface (finger contact surface) and located on an extension of the z-axis; the distance L1 of BO is 90 mm; the distances of AB and BC are 10 mm, respectively; the refractive index of the transparent base 7 is 1.5; and the curvature radius r is 10 mm.

Figure 5:
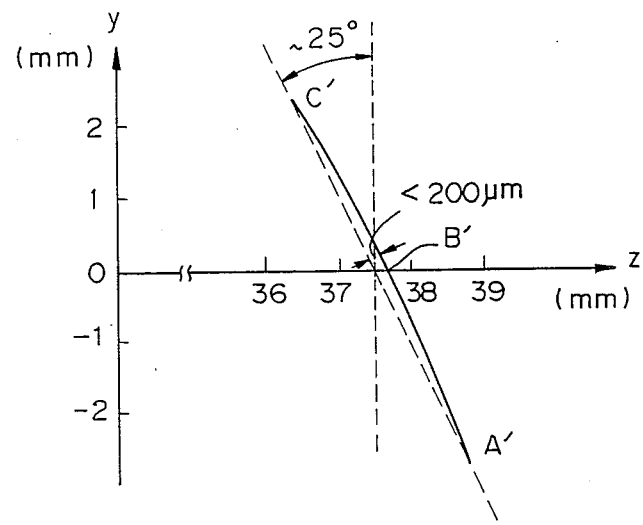
FIG. 5 is a diagram illustrating a position of the image determined by a calculation.

FIG. 5 illustrates the results of calculation for the change of the image obtained on the sensor surface. According to FIG. 5, the distance L2 of OB' is about 37.5 mm, and although the original position (flat surface) of the image is as indicated by the dashed line, the image according to the results of the calculation is as indicated by the solid line including points A', B' and C'. At the point B', the image is deviated in the direction of Z-axis by 200 $\mu$ or less. Nevertheless, such a small deviation falls within a focal depth of the lens, so that the whole fingerprint of a single finger can be entirely focused on the sensor surface by a single spherical convex lens.

Figure 6:
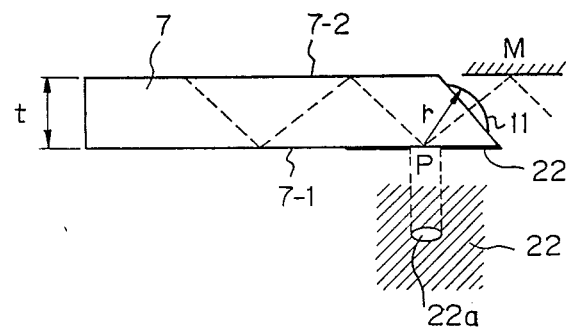
FIG. 6 is a schematic side view illustrating an embodiment of a total reflection preventing means having an aperture.

FIG. 6 illustrates an embodiment of the total reflection preventing means (iris diaphragm) 22 having the opening aperture 22a. A thickness of the transparent base 7 is selected in such a manner that the center P of curvature radius of the convex lens 11 is located just on one of surfaces (i.e., the lower surface 7-1) opposite to the fingerprint detection portion on the upper surface 7-2 of the transparent base 7, and an oblique aperture 22a (the area where the total reflection preventing film is not formed) is formed on a total reflection preventing film 22. Therefore, the light incident to the area of the oblique aperture is totally reflected. On the other hand, the light incident to the outside area of the oblique aperture cannot be reflected and is absorbed by the film portion. The reason why the aperture should have an oblique-shape is that the optical beam is inclined with respect to the reflection surface. Of course, such an oblique aperture operates in the same manner as the circular-shaped opening aperture in a general optical system.

Figure 7:
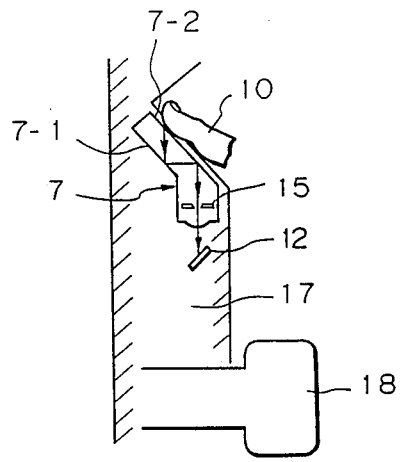
FIG. 7 is a schematic view of a door providing therein with a fingerprint detection apparatus of this invention.

FIG. 7 illustrates an example which uses an uneven surface (fingerprint) data detection apparatus according to the present invention. Where personnel entrance control should be conducted by identifying the fingerprints of individual persons, it is preferable to situate a fingerprint data detection apparatus in a door, particularly to completely insert it within the region defined by a thickness of the door, to attain both an easy operation and a preferred appearance. As shown in FIG. 7, a transparent base 7 is made in such a manner that a part thereof is bent and buried in the door 17 in the vicinity of the knob 18. The optical system for entering fingerprint image data to the image sensor 12 thus can be arranged as shown without affecting the appearance of the door 17. To conduct the entrance control, all that is necessary is to place a finger on the fingerprint contact surface of the transparent base 7 of the door. In FIG. 7, the same reference numerals indicate the same parts as in the embodiments as mentioned above.

Figure 8:
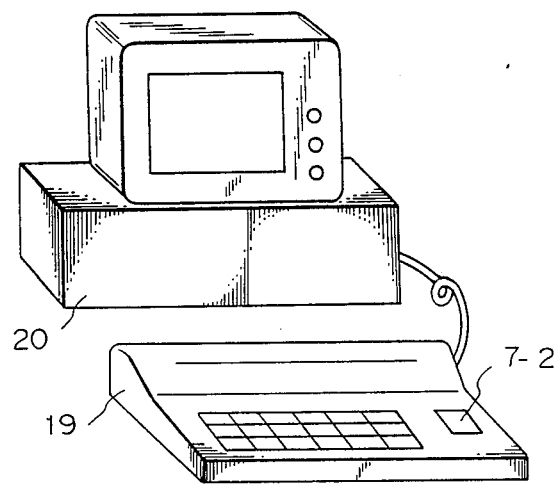
FIG. 8 is a perspective view of a computer keyboard on which a fingerprint detection apparatus of this invention is mounted.

FIG. 8 illustrates another application example which uses a fingerprint data detection apparatus of this invention to identify a person able to access a data base in a computer system. In this case, it is preferable not to provide an independent fingerprint data input apparatus, but to incorporate a fingerprint data input apparatus in a keyboard, to obtain both an easy operation and a preferred appearance. In the example shown in FIG. 8, reference numeral 19 indicates a keyboard and reference numeral 20 indicates a terminal apparatus of the computer.

Figure 9:
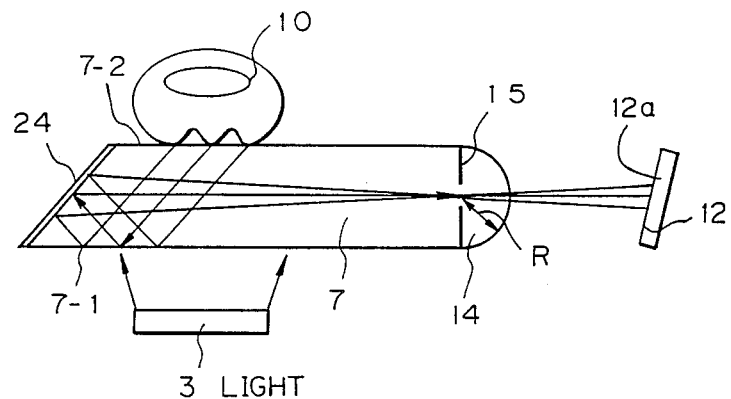
FIG. 9 is a side view of another embodiment of an optical system of a fingerprint detection apparatus of this invention.

FIG. 9 is a side view of another embodiment of an optical system of a fingerprint detection apparatus of this invention, wherein the light from the fingerprint contact surface 7-2 is once totally reflected by the lower surface 7-1 and then reflected by a mirror 24 formed on an inclined end face of the transparent body 7, so that the light reflected by the mirror 24 becomes substantially parallel to the upper fingerprint contact surface 7-2 and to the lower surface 7-1 of the transparent body 7, and passes therethrough to the semi-spherical lens 14, which can be adhered to the other end face of the transparent body 7. Also, the opening aperture 15a of the iris diaphragm 15 is positioned at the center of curvature of the radius of the semi-spherical lens 14.

Figure 10:
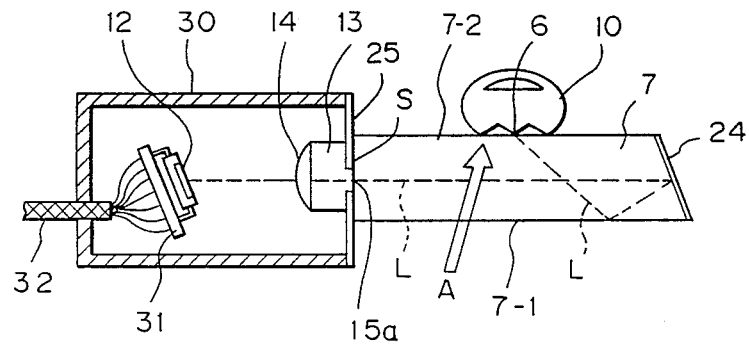
FIG. 10 shows still another structure of a fingerprint detection apparatus of this invention.

FIG. 10 shows still another structure of a fingerprint detection apparatus of this invention. In this embodiment, the light from the fingerprint contact surface 7-2 is once totally reflected by the opposite surface 7-1 and then reflected by a mirror 24 formed on the inclined face of the transparent body 7, in the same manner as in the embodiment of FIG. 9.

A metal plate 25 having an aperture 15a is adhered by a suitable optical adhesion to the other end face of the transparent body 7, i.e., to the surface S perpendicular to L, in such a manner that the aperture 15a is positioned on L. Here, L is defined as an optical axis of the light transmitted from the fingerprint contact surface 7-2 and reflected by the mirror 24.

A lens having a cylindrical portion 13 and a convex lens portion 14 similar to the lens shown in FIG. 2 is adhered by a suitable optical adhesion to the metal wall 25 from the opposite side of the transparent body 7, so that the center of curvature radius of the convex lens portion 14, is positioned at the aperture 15a.

An optical magnetical shield box 30 has an open end and accommodates therein the image sensor 12, such as a CCD mounted on a printed circuit substrate 31. A shield box 30 is integrally connected to the metal plate 25 in such a manner that the opened end of the shield box 30 is closed by the metal plate 25 and the light receiving surface of the sensor 12 is inclined by a certain angle to the optical axis L. A signal from the image sensor 12 is externally output from the shield box 30 by a cable 32.

Since the image sensor 12 is optically opened to the outside through only a very small pin-hole, i.e., the aperture 15, the shield box 30 is completely shielded or closed, and thus magnetic influences or unfavorable light affecting the image sensor 12 can be effectively avoided.

Figure 11:
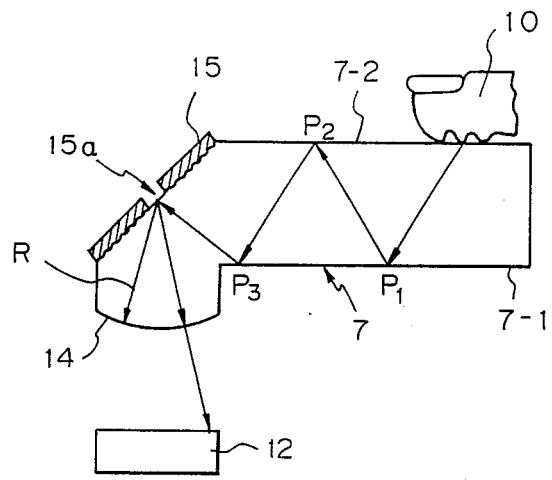
FIG. 11 is a side view of an embodiment of a transparent body used in a fingerprint detection apparatus of this invention.

FIG. 11 illustrates an embodiment of a transparent body 7 used in a fingerprint detection apparatus of this invention. In this embodiment, the transparent body 7 has a rough surface 15 inclined by 45° with respect to the finger contact surface 7-2, so that the transparent body 7 has a substantially L-shaped configuration. The surface 15 has a smooth portion which defines an aperture 15a positioned at the center of curvature of the radius of the focussing lens 14. The rough surface 15 prevents the total reflection, but absorbs the light incident thereon. On the other hand, the aperture 15a allows a total reflection, and therefore, the light the finger contact surface 7-2 is totally reflected by the opposite surface 7-1 at P1, by the surface 7-2 at P2, by the surface 7-1 at P3, and then by the inclined surface at 15a, since the light incident on the rough area 15 is scattered and does not enter the focussing lens 14, and only the light incident on the smooth area (i.e., the aperture) 15a is totally reflected and enters the image sensor 12 through the focussing lens 14.

Figure 12:
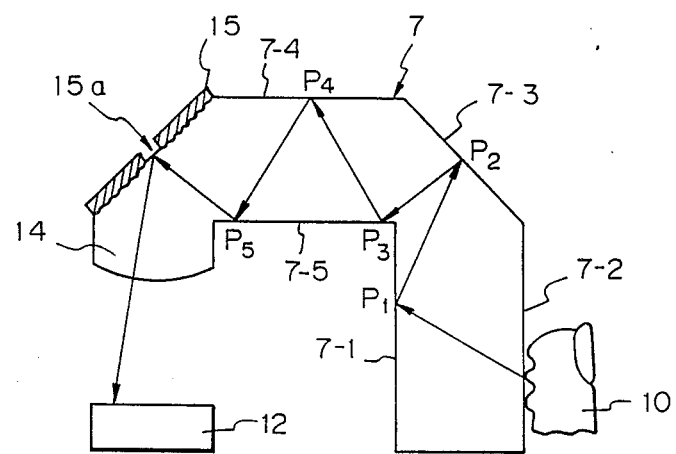
FIG. 12 is a side view of another transparent body used in a fingerprint detection apparatus of this invention.

FIG. 12 illustrates another transparent body, wherein the transparent body 7, is bent twice by 90° into a substantially J-shaped configuration. That is, the transparent body 7 has a first total reflection (or mirror) surface 7-3 inclined by 45° with respect to the finger contact surface 7-2, a successive second total 5 reflection surface 7-4 inclined by 45° to the first total reflection surface 7-3, an opposite total reflection surface 7-5 parallel to the second surface 7-4, and a rough surface 15 inclined by 45° to the third surface 7-3.

In the above embodiments, the total reflection preventing means may be constituted by either one of a metal plate, a metal film formed by, e.g., vaporde-position, a rough surface, a light absorbing paint film, or the like.

Thus the surface 15 has a smooth portion which defines an aperture 15a positioned at the center of curvature of the radius of the focussing lens 14. Therefore, the light from the finger contact surface 7-2 is totally reflected by the opposite surface 7-1 at P1, by the surface 7-3 at P2, by the surface 7-5 at P3, by the surface 7-4 at P4, again by the surface 7-5 at P5, and then by the inclined surface at 15a. The light enters to the rough area 15 is scattered and does not enter the focussing lens 14, and only the light input to the smooth area (i.e., the aperture) 15a is totally reflected and enters the focussing lens 14 and is focussed on the image sensor 12.

Figure 13:
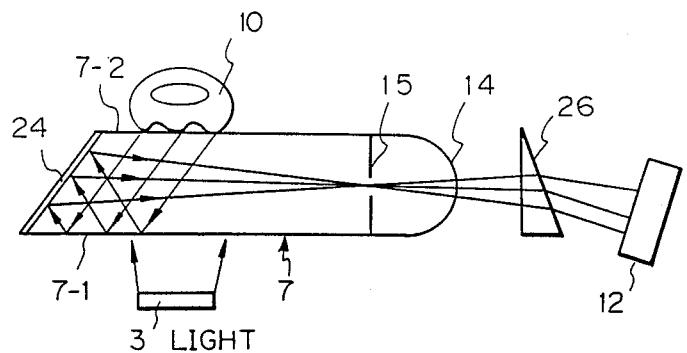
FIGS. 13, 14, and 15 are views of respective embodiments of the optical systems of this invention using a prism.
Figure 14:
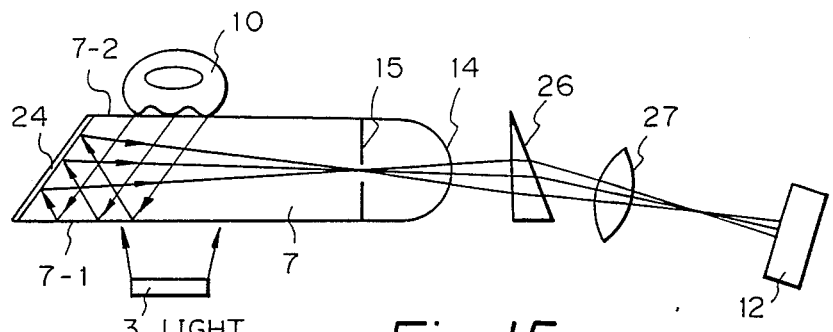
Figure 15:
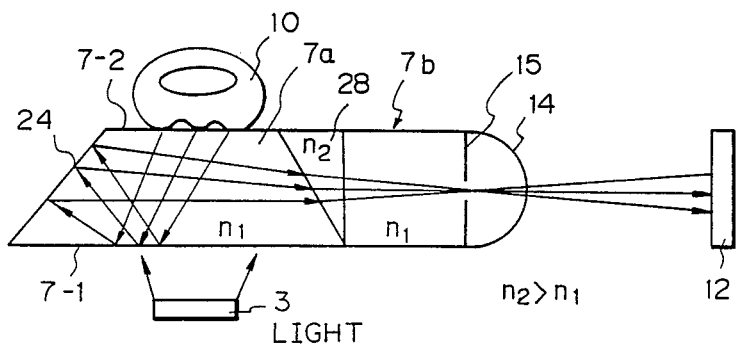

FIGS. 13, 14, and 15 illustrate embodiments of the fingerprint detection apparatus, particularly an optical system using a prism. The embodiment shown in FIG. 13 is similar to that of FIG. 9, except that a prism 26 is arranged between the focussing lens 14 and the image sensor in such a manner that the optical length of a light path incident on the image sensor 12 becomes uniform in the whole region of the fingerprint image. Therefore, the image obtained on the sensing surface of the image sensor 12 has less aberrations or distortions.

The embodiment shown in FIG. 14 is similar to that of FIG. 13, except that a second lens 27 is further arranged between the prism 26 and the image sensor 12 in such a manner that the light corrected by the prism 26 is further focussed by the this lens 27 and enters to the image sensor 12.

In the embodiment shown in FIG. 15, a prism portion 28 is incorporated in the transparent base 7. This prism portion 28 has a refraction index $n_2$ which is larger than a refraction index $n_1$ of the transparent base 7. Therefore, the light (which comes from the fingerprint contact surface 7-2 and is at least once totally reflected by the lower surface 7-1) is corrected before being focussed by the focussing lens 14, in such a manner that the length of light path becomes uniform in the whole region of the fingerprint image. Therefore, the image obtained on the sensing surface of the image sensor 12 has less aberrations or distortions.

Figure 16:
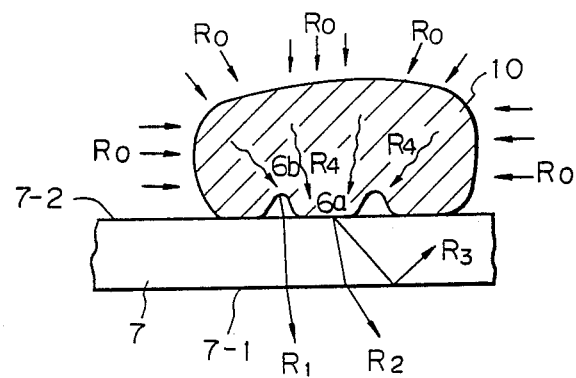
FIG. 16 is a schematic cross-sectional view illustrating a principle structure of a further embodiment of a fingerprint detection apparatus of this invention.

FIGS. 16 to 20 are views illustrating a further embodiment of a fingerprint detection apparatus of this invention. If the object to be detected and having an uneven surface having projected portions and recessed portions is transparent, or at least partially light transmissible, and has a light scattering surface (a human finger is such an object), a light source for illuminating the uneven surface can be located at the side of upper surface of the transparent body 7, as shown in FIG. 16. In this case, the uneven surface is illuminated by the light transmitted through the object (finger) itself, so that a part of the light can be discharged from the projected portions (P) and the rest can be discharged from the recessed portions (Q), in the same manner as in the previous embodiments.

Figure 17:
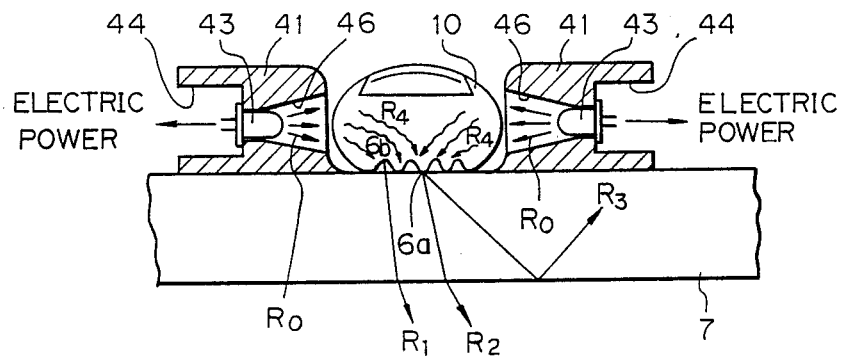
FIG. 17 is a cross-sectional view illustrating in detail the embodiment of the fingerprint detection apparatus shown in FIG. 16.
Figure 18:
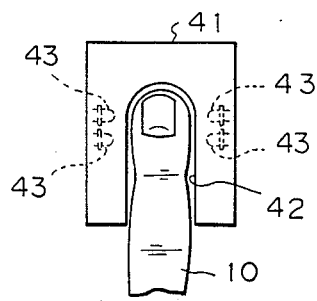
FIGS. 18 and 19 are top and perspective views of a guide member used in the embodiment shown in FIG. 17.
Figure 19:
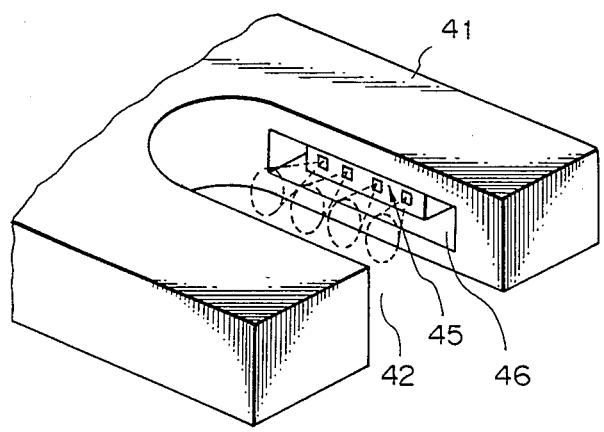

In FIGS. 17, 18 and 19, a substantially U-shaped guide member 41 is provided on the upper fingerprint contact surface 7-2 of the transparent base 7. The guide member 41 has a guide opening 42 in which a finger 10 is inserted. Since the U-shaped guide member 41 is fixed to the upper surface 7-2 of the transparent base 7, when a finger is inserted in the guide opening 42, the fingerprint comes into contact with the surface 7-2 at a predetermined position. A pair of light sources 43, such as laser diodes or LED, small lamps or the like, are inserted and fixed in a pair of recesses 44 as shown in FIG. 17. Each of the recesses 44 is preferably communicated with a cone-shaped opening 46, to widen the illuminating region toward the inside of the U-shaped guide member 41. A pair of or a plurality of pairs of such light sources 43 may be provided. Laser diode or LED arrays 45, as shown in FIG. 19 also can be used. Thus the fingerprint on the contact surface 7-2 is uniformly illuminated by the light coming from the respective sides of the U-shaped guide member 41 and passing through the finger itself. The light used in this embodiment is preferably selected so that the light has a certain wavelength to show a high light transmissible characteristics.

Figure 20:
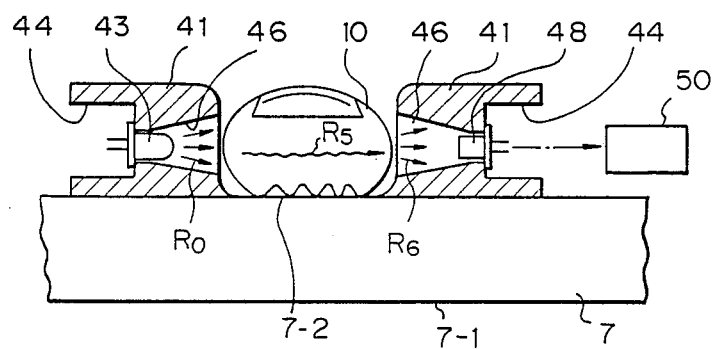
FIG. 20 is a cross-sectional view of an embodiment of a fingerprint detection apparatus which is also intended for use as an optical living body detecting apparatus; and, FIGS. 21 and 22 are schematic views illustrating uneven surface data detection apparatuses known in the prior art.
Figure 21:
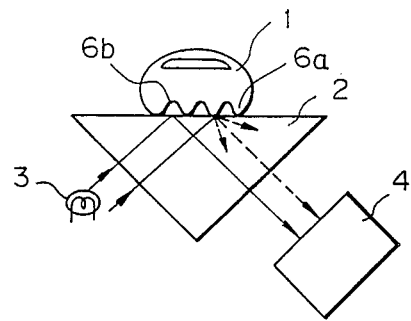
Figure 22:
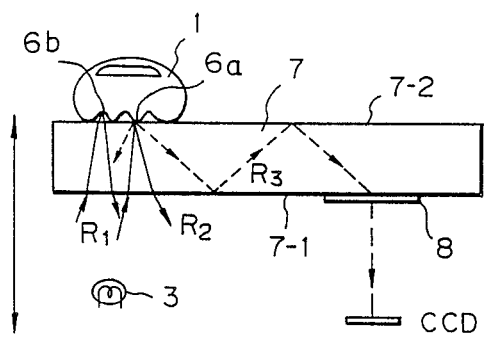

In FIG. 20, the U-shaped guide member 41 is incorporated with a pair of light emitting elements 43, such as LED's as mentioned above, and a light receiving element 48. The light emitted from the light emitting elements 43 passes through the finger placed on the fingerprint contact surface 7-2 and is received by the light receiving element 48. A part of the light emitted from the light emitting elements 43 illuminates the fingerprint through the finger itself. As is well known, a condition of the blood, such as a distribution of the red blood corpuscles of a part of a human body, such as a finger, is subjected to periodical changes due to blood pulsation. Thus the amplitude of the light received by the light receiving element 48 is also periodically changed, and therefore, if a human finger is correctly placed on this apparatus, this can be detected before the detection of a finger print. Thus if the light receiving element 48 receives a certain periodically changing amplitude of the light, it can be considered that a human finger is correctly inserted to the guide member 41, and thereafter, the detection of a fingerprint can be started.

For example, if a finger is incorrectly inserted, such as inserted while wearing a glove, or if an other article is inserted to the guide member 41, such a periodically changing amplitude of the light cannot be received by the light receiving element 48. In this case, a detection of a fingerprint can not be started.

U.S. Pat. No. 4,728,186 discloses a personal identification system, such as a system for discriminating detected data and the registered data beforehand, and the same system can be used here.

We claim:

1. An uneven surface data detection apparatus for detecting an uneven surface having projected portions and recessed portions, comprising:
    a transparent base having first and second surfaces, at least a part of said first surface defining an uneven surface contact portion;
    a light source for illuminating said uneven surface on said uneven surface contact portion, said light source simultaneously illuminating said projected portions and recessed portions of said uneven surface, so that the light derived from the recessed portions enters to said transparent base and comes out thereof and, at least a part of the light derived from the projected portions is totally reflected at least one time by the second surface opposite to said first surface;
    a focussing lens integrally formed on or integrally adhered to said transparent base, said focussing lens being located at a position for drawing said totally reflected light out of said transparent base; and
    an image sensor arranged outside said transparent base for detecting an image of said uneven surface including said projected and recessed portions.

2. An apparatus according to claim 1, wherein said focussing lens comprises a convex lens.

3. An apparatus according to claim 2, said apparatus further comprising:
    an iris diaphragm having an aperture, said iris diaphragm being arranged in such a manner that said aperture is located at a position corresponding to a center of curvature radius of said convex lens, so that the light can be totally reflected at an area of said aperture.

4. An apparatus according to claim 3, wherein said iris diaphragm comprises a metal plate arranged in or adhered to said transparent base.

5. An apparatus according to claim 3, wherein said iris diaphragm comprises a metal film formed by vapor-deposition of a metal on said transparent base.

6. An apparatus according to claim 3, wherein said iris diaphragm comprises a rough surface formed on said transparent base.

7. An apparatus according to claim 3, wherein said iris diaphragm is formed by a light absorbing paint film coated on said transparent base.

8. An apparatus according to claim 3, wherein said iris diaphragm is formed on one of said first and second surfaces of said transparent base.

9. An apparatus according to claim 3, wherein said iris diaphragm is arranged inside of said transparent base.

10. An apparatus according to claim 1, wherein said focussing lens is integrally formed with said transparent base as a part thereof.

11. An apparatus according to claim 1, wherein said focussing lens comprises a cylindrical portion having one end integrally connected to said transparent base and the other end integrally formed with a convex lens portion.

12. An apparatus according to claim 1, wherein said first and second surfaces are substantially parallel to each other and said transparent base has a third surface inclined to said first and second surfaces, and said focussing lens is formed on or adhered to said third surface of said transparent base.

13. An apparatus according to claim 12, wherein said first and second surfaces are substantially parallel to each other and said apparatus further comprising:
   a total reflection preventing film having an aperture located at a position corresponding to a center of curvature of a radius of said convex lens, and said total reflection preventing film and said aperture is formed on said third surface.

14. An apparatus according to claim 1, wherein said first and second surfaces are substantially parallel to each other and said transparent base has a third surface inclined to said first and second surfaces and said third surface is formed as a mirror surface, so that the light once totally reflected by said second surface is reflected by said mirror surface in such a manner that a propagation direction of the light reflected by said mirror surface is directed in the transparent base.

15. An apparatus according to claim 3, said apparatus further comprising:
   a shield box accommodating said image sensor, said shield box comprising a wall, a part of said wall being defined by said iris diaphragm.

16. An apparatus according to claim 15, wherein said iris diaphragm comprises a metal plate adhered to said transparent base and said convex lens is adhered to said metal plate from the inside of said shield box, in such a manner that said convex lens is integrally connected to said transparent base through said aperture.

17. An apparatus according to claim 1, wherein said first and second surfaces are substantially parallel to each of the and said transparent base has a third surface inclined to said first and second surfaces and said inclined third surface is formed as a total reflection surface or a mirror surface, so that the light at least once totally reflected by said second surface is reflected by said inclined third surface.

18. An apparatus according to claim 17, wherein said first and second surfaces are substantially parallel to each other and said transparent base has fourth and fifth surfaces substantially parallel to each other and substantially perpendicular to said second and first surfaces, respectively, and said inclined third surface is defined between said fourth and fifth surfaces, so that the light reflected by said inclined third surface is then totally reflected, in turn, by said fourth and fifth surfaces.

19. An apparatus according to claim 1, said apparatus further comprising:
   a prism arranged between said focussing lens and said image sensor so that the light drawn out of said transparent body passes through said prism.

20. An apparatus according to claim 1, wherein said transparent base comprises a prism portion therein, said prism portion has a refraction index which is different from that of said transparent base, so that the light at least once totally reflected by said second surface passes through said prism portion.

21. An apparatus according to claim 1, wherein said light source for illuminating said uneven surface is located at the side of said second surface opposite to said first surface on which said uneven surface contact portion is defined, so that the light illuminates the uneven surface through said transparent base.

22. An apparatus according to claim 1, wherein an object to be detected having said uneven surface is a light transmissible body and said light source for illuminating said uneven surface is located at the side of said first surface on which said uneven surface contact portion is defined. so that the light illuminates the uneven surface through said object.

23. An apparatus according to claim 22, wherein said object to be detected as said uneven surface having projected portions and recessed portions is a human finger having a fingerprint;
   said apparatus further comprising:
   a guide member provided on said first surface for guiding the finger onto said uneven surface contact portion, said guide member being incorporated with said light source so that the light illuminates the uneven surface through said finger.

24. An apparatus according to claim 23, wherein said guide member is incorporated with a pair of a light emitting element and a light receiving element, in such a manner that the light emitted from said light emitting element passes through said finger placed on said uneven surface contact portion and is received by said light receiving element, and a part of the light emitted from said light emitting element illuminates the uneven surface through said finger.

25. An apparatus according to claim 24, wherein said guide member is substantially U-shaped.

26. An uneven surface data detection apparatus for detecting an uneven surface having projected portions and recessed portions, comprising:
   a transparent base having first and second surfaces, at least a part of said first surface defining an uneven surface contact portion;
   a light source for illuminating said uneven surface on said uneven surface contact portion, said light source simultaneously illuminating said projected portions and recessed portions of said uneven surface, so that the light derived from the recessed portions enters to said transparent base and comes out thereof and at least a part of the light derived from the projected portions is totally reflected at least one time by the second surface opposite to said first surface;
   first focussing lens integrally formed on or integrally adhered to said transparent base, said first focussing lens being located at a position for drawing said totally reflected light out of said transparent base;
   an image sensor arranged outside said transparent base for detecting an image of said uneven surface including said projected and recessed portions; and
   second focussing lens arranged between said first focussing lens and said image sensor so that the light drawn out of said transparent body passes through said second focussing lens.

27. An apparatus according to claim 26, said apparatus further comprising a prism arranged between said first and second focussing lens.

* * * * *

UNITED STATES PATENT AND TRADEMARK OFFICE
CERTIFICATE OF CORRECTION

Page 1 of 2

PATENT NO. : 4,924,085

DATED : May 8, 1990

INVENTOR(S) : Masayuki KATO et al.

It is certified that error appears in the above-identified patent and that said Letters Patent is hereby corrected as shown below:

Col. 1,  line 8, after "as" insert --a--.

Col. 3,  line 15, after "In" insert --a--.

Col. 6,  line 7, change "face" to --fact--;
         line 12, after "input" insert --to--;
         line 48, after "one of" insert --the--.

Col. 8,  line 18, after "light" insert --incident on--;
         line 50, change "enters to" to --incident on--.

Col. 9,  line 1, delete "to";
         lines 11 and 22, after "of" insert --the--;
         line 52, change "to show a" to --affording--.

Col. 10, line 1, change "finger print" to --fingerprint--;
         line 7, change "an other" to --another--;
         line 11, change "can not" to --cannot--.

Col. 11, line 45, change "of the" to --other--.

UNITED STATES PATENT AND TRADEMARK OFFICE
CERTIFICATE OF CORRECTION

PATENT NO. : 4,924,085

DATED : May 8, 1990

INVENTOR(S) : Masayuki KATO et al.

It is certified that error appears in the above-identified patent and that said Letters Patent is hereby corrected as shown below:

Col. 12, line 14, change "." to --,--.

Signed and Sealed this

Twenty-fifth Day of June, 1991

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,924,085

DATED : May 8, 1990

INVENTOR(S) : Masayuki Kato, et al

It is certified that error appears in the above-identified patent and that said Letters Patent is hereby corrected as shown below:

On the title page, item [75] Inventors:, change "Masayuji Kato" to --Masayuki Kato--.

Signed and Sealed this

Eighth Day of October, 1991

*Attest:*

HARRY F. MANBECK, JR.

*Attesting Officer*  *Commissioner of Patents and Trademarks*